(12) United States Patent
Lithgow

(10) Patent No.: US 6,422,238 B1
(45) Date of Patent: Jul. 23, 2002

(54) HEADGEAR

(75) Inventor: Perry D. Lithgow, Glenwood (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/482,718

(22) Filed: Jan. 12, 2000

(30) Foreign Application Priority Data

Jan. 12, 1999 (AU) .............................................. PP8121

(51) Int. Cl.[7] .......................... A62B 18/00; A62B 18/08
(52) U.S. Cl. ............................ 128/207.11; 128/207.17; 128/205.25; 128/206.21; 128/206.24; 128/206.12; 128/206.13; 128/206.28
(58) Field of Search ....................... 128/205.25, 206.21, 128/206.24, 206.12, 206.13, 207.11, 206.28, 207.17; 2/173

(56) References Cited

U.S. PATENT DOCUMENTS 3,056,402 A   10/1962   Dickinson
5,035,006 A * 7/1991   Hetz et al. .................... 2/209.1
5,069,205 A * 12/1991  Urso ...................... 128/201.24
5,237,986 A   8/1993   Seppala et al.
5,441,046 A * 8/1995   Starr et al. ............. 128/207.11
5,492,116 A * 2/1996   Scarberry et al. ....... 128/206.24
5,517,986 A * 5/1996   Starr et al. ............. 128/206.24
5,542,128 A * 8/1996   Lomas .......................... 2/173

* cited by examiner

Primary Examiner—John G. Weiss
Assistant Examiner—Mital Patel
(74) Attorney, Agent, or Firm—Pillsbury Winthrop LLP

(57) ABSTRACT

Headgear (20) for securing a respiratory mask (12) to a patient incorporates a quick release arrangement. The headgear has at least one strap (22,24) extending from each side of the mask, the straps being releasably fastened rearwards of the patient's face to secure the mask. The headgear further includes release means in the form of a pull cord (41) attached to an overlying strap (22) at its region of fastening to the underlying strap (24) an guided forward to be gripped at the front of patient. Pulling forward to the pull tab (45) of the cord (41) separates the fastening (28) between the straps (22,24) and pulls the mask away from the patient's face.

22 Claims, 3 Drawing Sheets

HEADGEAR

BACKGROUND OF INVENTION

This invention relates to headgear for securing a mask to a human face. The invention has particular application for patent gas delivery systems of the kind used in the treatment of respiratory disorders such as Obstructive Sleep Apnea (OSA) and the like.

There is a need to provide a system whereby a respiratory mask being worn by a person can be removed quickly and easily in the event of an emergency. Such an emergency may occur for example through anxiety of the person, failure of a gas delivery system or where the person has vomited into the gas mask.

U.S. Pat. No. 5,441,046 assigned to Respironics Inc. discloses buckle-type connectors pivotably attached to both sides of the mask shell. A strap passes around the rear of the wearer's head and attaches to the buckles. Pivoting of the buckles by means of a cord will release the engagement of the strap with one of the buckles.

Later U.S. Pat. No. 5,492,116, also assigned to Respironics Inc., has a strap which passes from one side of the mask shell around the rear of the wearer's head and attaches to the other side of the mask shell by VELCRO™ type fasteners. This arrangement does not provide sufficiently swift and simple removal of the mask by an anxious patient.

There is a need for a convenient and effective alternative.

SUMMARY OF THE INVENTION

The invention resides it respiratory mask-securing headgear for securing to the face of a wearer a respiratory mask having a fist side and an opposite second side, the headgear including at least one strap extending from each of the first and second sides of the mask, the straps in use being releasably fastened at a region rearwards of the facial region of the wearer by fastening means so as to secure the mask, the headgear further including release means acting on the fastening means and in use extending forward of the fastening means such that the release means may be gripped from substantially the front of the wearer and actuated to release the fastening means and thereby allow removal of the headgear from the wearer.

Preferably the fastening means is located in use at the rear of the head of the wearer.

Preferably, the fastening means includes a hook fastener attached on an inner surface of an overlying one of said straps, wherein said release means is attached to said overlying strap at said fastening means and acts to pull said overlying strap away from said other strap to release the fastening means.

Preferably also, the release means is a release cord attached at one end thereof to the inner surface of the overlying strap, wherein said overlying strap has one or more guides through which the release cord passes, such that a distal end of the release cord is located at the front of the wearer and may be pulled to actuate release of the fastening means.

BRIEF DESCRIPTION OF THE DRAWINGS

Preferred embodiments of the invention will now be described with reference to a particular embodiment in which the mask forms par of a patient gas delivery system. It is not intended that the invention be limited to this embodiment and many other embodiments and applications will be apparent to those skilled in the art. The invention is described with reference to the accompanying drawings in which.

DETAILED DESCRIPTION OF THE PREFERRED EMBODIMENTS

Figure 1:
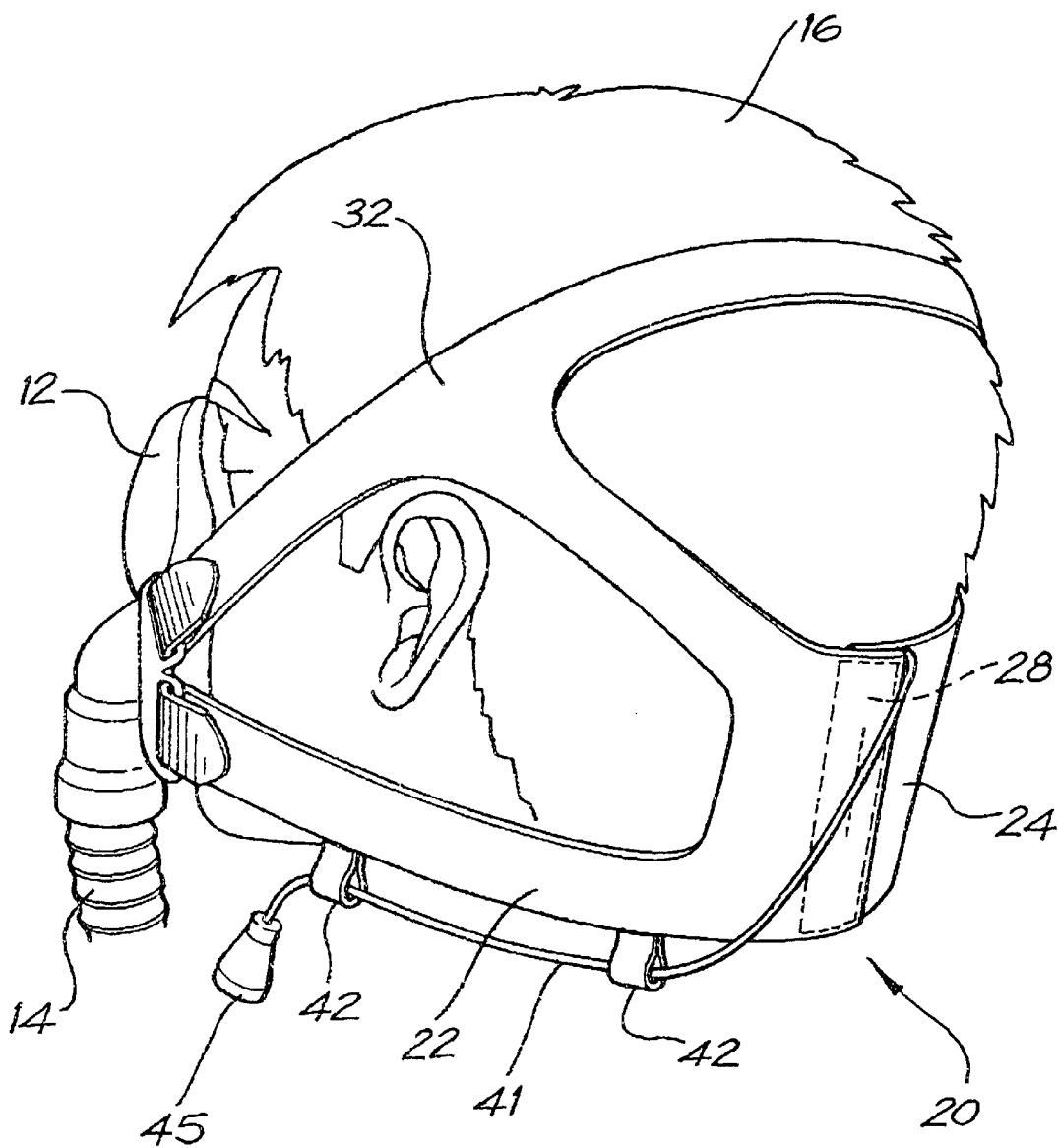
FIG. 1 shows the headgear according to the invention in situ in a fastening position.

FIG. 1 shows a patient gas delivery mask 12 with attached gas delivery conduit 14, in situ on the head of a patient 16. The gas delivery mask is secured to the patient by headgear 20 according to the present invention.

Figure 2:
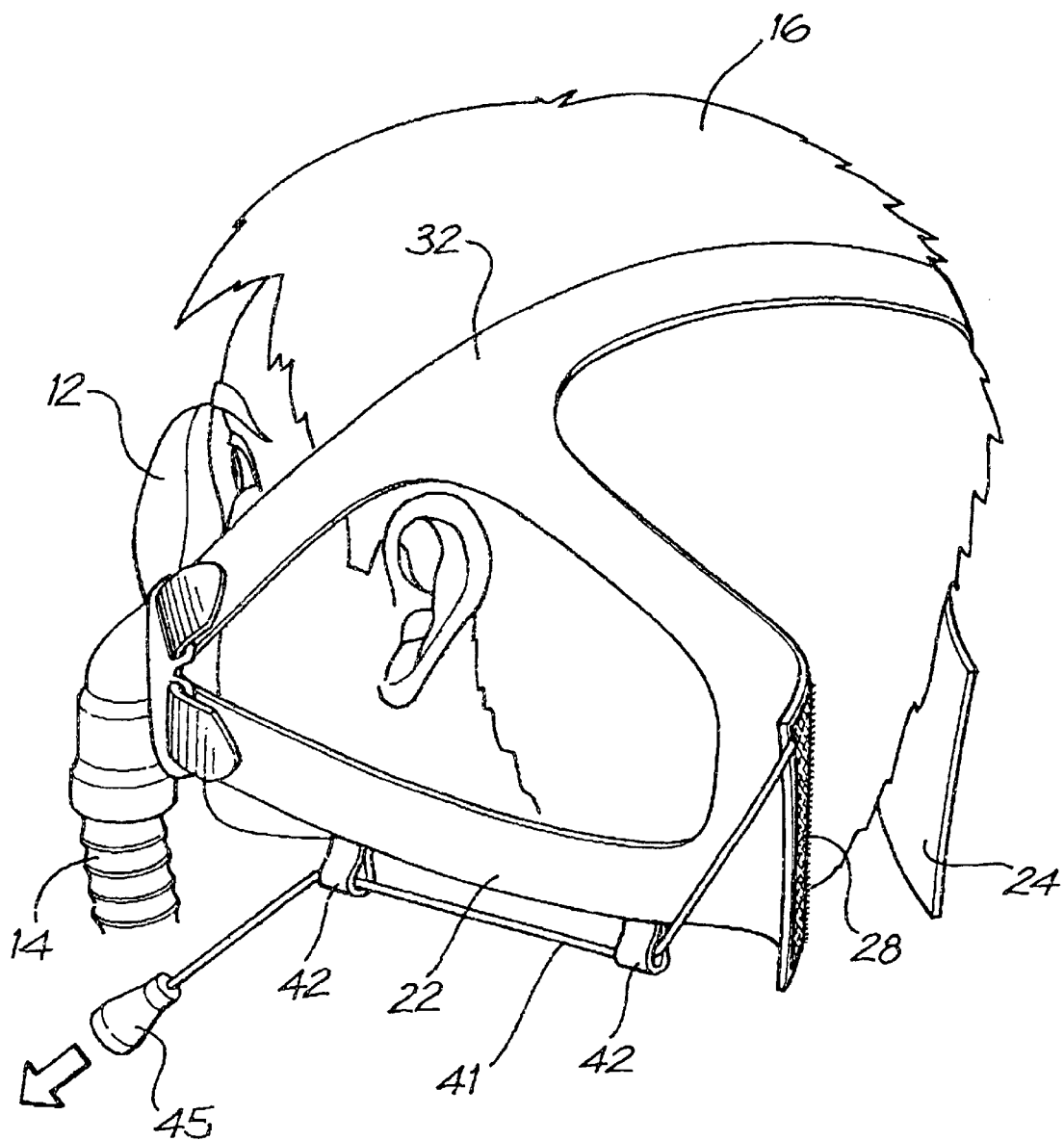
FIG. 2 shows headgear according to the invention in situ in a release position.

The headgear 20 has a strap 22 extending from the mask 12 on the patient's left hand side. Extending from the right hand side of the mask is a second strap 24 (FIG. 2). The straps 22, 24 are preferably secured to the mask in an adjustable manner to enable the headgear to fit on a wide range of head sizes. The straps 22, 24 are coined by a hook fastener 28 such as VELCRO™ brand tape. The fastener 28 is shown located in the centre of the rear of the head of the patient 16 but may also be located at the side of the patient s head, rearwards of the facial region of the wearer. Ancillary straps 32 may also be provided to assist in locating the headgear on the patient before the fastener 28 is fastened. The stows 32 also provide a more secure fitting of the mask and increased comfort to the patient.

Figure 3:
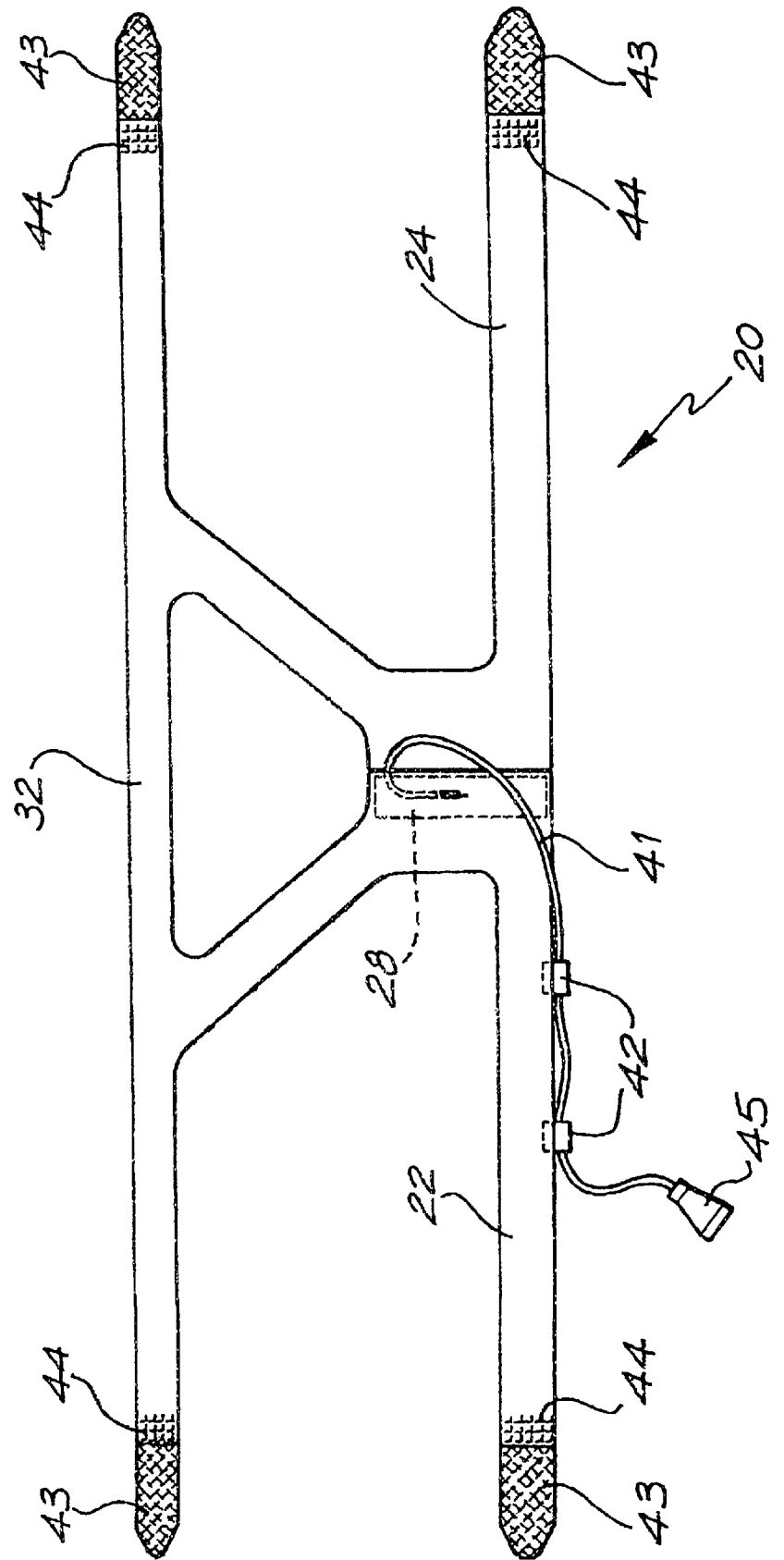
FIG. 3 is a plan view of the headgear laid flat, before attachment to the patient mask.

The straps 22, 24, 32 are preferably made of a soft material, such as closed cell foam, that easily conforms to the shape of the patient's head while providing sufficient tensile strength to support the mask on the patient's face. The straps preferably have an outer covering of the material at can serve as loop material for the hook and loop fastener 28. In this way, the hook portion of the fastener can secure onto any part of the straps allowing greater adjustability and ease of operation. In addition, the straps can terminate at tile mask end in a short section of hook material 43 that can pass through an attachment slot of the mask and hen secure to the loop material of the strap with maximum adjustability (see FIG. 3). These sections of hook material may be attached to the straps by any suitable means, for example ultrasonic welding 44 or stitching. All of the straps 22, 24, 32 preferably have a soft fabric coating on their inner surface to provide greater comfort to the patient.

Attached to the overlying strap 22 in the region of the fastener 28 is a release cord 41 extending from the fastener 28 through guide loops 42 towards the face of the patient. The distal end of cord 41 to terminates in a pull tab 45 that preferably sits forward of the shoulder of the patient the tab 45 is of a size that allows it to be easily located and gripped in an emergency by an attending person or by the patient.

To remove the headgear from the patient the pull tab 45 is gripped and the cord 41 is pulled forward of the patient This pulls the overlying strap 22 away from the strap 24 beneath it and separates the fastener 28. In the same action, the cord 41 is pulled further from the patient, thereby removing the headgear 20 and mask 12 and allowing the patient to breathe normally or be attended to as required.

The cord 41 is preferably connected at an upper region of the fastener 28 but may be connected in any way such that when the cord is pulled in an appropriate direction the fastener is released. Preferably, the cord 41 is stitched to the inner side of the overlying strap 22 and then brought outside the strap and fed through the guide loops 42. The force exerted when the cord is pulled thus as on an edge of the strap to pull the hook material directly away from the underlying loop material.

Because the fastener is located away from The face of the patient, a force exerted on the fastener 28 by the release cord 41 acts on the overlying strap 22 only, to separate it from the underlying strap 24. The action of the release cord 41 helps retain the underlying strap 24 firmly against the patient's head. The operation of the release cord 41 is therefore more direct than if the fastener were located near the face of the patient in which case the release cord would first act on both straps to extend them away from the patient's head before acting to separate them, The most preferred location for the fastener 28 is the rear of the patient's head because then the cord 41 works in exact opposition to the underlying strap 24. The construction of present invention has the added advantage that the releasing of the fastener 28 and the removal of the mask from the patient can be performed with one forward pull of the release cord.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. A respiratory mask and headgear combination comprising a respiratory mask being a patient gas delivery mask having a first side and an opposite second side, and respiratory mask-securing headgear for securing said mask to the face of a wearer, the headgear including at least one strap extending from each of the first and second sides of the mask, the straps in use being releasably fastened at a region rearwards of the facial region of the wearer by fastening means so as to secure the mask, the headgear further including a release actuator acting on the fastening means and in use extending forward from the fastening means to a position substantially at the front of the wearer such that the release actuator may be gripped at substantially the front of the wearer and actuated to release the fastening means and thereby allow removal of the headgear from the wearer.

2. A respiratory mask and headgear combination according to claim 1 wherein the fastening means is located in use at the rear of the wearer's head.

3. A respiratory mask and headgear combination according to claim 1 wherein the fastening means includes a hook fastener attached to one of said straps.

4. A respiratory mask and headgear combination according to claim 3 wherein the hook fastener releasably fastens to a covering of said other strap.

5. A respiratory mask and headgear combination according to claim 1 wherein an overlying one of said straps overlies the other of said straps at said fastening means, wherein said release actuator is attached to said overlying strap at said fastening means and acts to pull said overlying strap away from said other strap to release the fastening means.

6. A respiratory mask and headgear combination according to claim 5 wherein said fastening means includes a hook fastener on an inner surface of said overlying strap.

7. A respiratory mask and headgear combination according to claim 6 wherein said release actuator is a release cord attached at one end thereof to said inner surface of the overlying strap.

8. A respiratory mask and headgear combination according to claim 7 wherein said release actuator is attached at an upper portion of said inner surface.

9. A respiratory mask and headgear combination according to claim 1 when used as a part of a patient gas delivery system for treatment of a respiratory disease.

10. A respiratory mask and headgear combination comprising a respiratory mask being a patient gas delivery mask having a first side and an opposite second side, and respiratory mask-securing headgear for securing said mask to the face of a wearer, the headgear including at least one strap extending from each of the first and second sides of the mask, the straps in use being releasably fastened at a region rearwards of the facial region of the wearer by fastening means so as to secure the mask, the headgear further including a release actuator acting on the fastening means and in use extending forward from the fastening means to a position substantially at the front of the wearer such that the release actuator may be gripped at substantially the front of the wearer and actuated to release the fastening means and thereby allow removal of the headgear from the wearer, wherein an overlying one of said straps overlies the other of said straps at said fastening means, wherein said release actuator is a release cord attached to said overlying strap at said fastening means and acts to pull said overlying strap away from said other strap to release the fastening means and, wherein the overlying strap has one or more guides through which the release cord passes, such that a distal end of the release cord is located in use at the front of the wearer and may be pulled to actuate release of the fastening means.

11. A respiratory mask and headgear combination according to claim 10 wherein in use a force acting on the headgear due to pulling of the cord acts to retain said other strap against the wearer's head whilst pulling away the overlying strap.

12. A respiratory mask and headgear combination according to claim 11 wherein in use further pulling of the cord in substantially the same direction acts to remove the headgear and mask from the wearer.

13. A respiratory mask and headgear combination according to claim 11 the fastening means is located in use at the rear of the wearer's head.

14. A respiratory mask and headgear combination comprising a respiratory mask being a patient gas delivery mask having a first side and an opposite second side, and respiratory mask-securing headgear for securing said mask to the face of a wearer, the headgear including at least one upper strap adjustably attached to the first and second sides of the mask and in use passing around an upper portion of the wearer's head, and further including at least one lower strap extending from each of the first and second sides of the mask to a lower rear portion of the wearer's head, the lower straps in use being releasably fastened at a region rearwards of the facial region of the wearer by fastening means so as to secure the mask, the headgear further including a release actuator acting on the fastening means and in use extending forward from the fastening means to a position substantially at the front of the wearer such that the release actuator may be gripped at substantially the front of the wearer and actuated to release the fastening means and thereby allow removal of the headgear from the wearer.

15. A respiratory mask and headgear combination according to claim 14 wherein the fastening means is located in use at the rear of the wearer's head.

16. A respiratory mask and headgear combination according to claim 15 wherein an overlying one of said lower straps overlies the other of said lower straps at said fastening means, wherein said release actuator is attached to said overlying strap at said fastening means and acts to pull said overlying strap away from said other strap to release the fastening means.

17. A respiratory mask and headgear combination according to claim 16 wherein said fastening means includes a hook fastener on an inner surface of said overlying strap.

18. A respiratory mask and headgear combination according to claim 17 wherein said release actuator is a release cord attached at one end thereof to said inner surface of the overlying strap.

19. A respiratory mask and headgear combination according to claim 18 wherein said release actuator is attached at an upper portion of said inner surface.

20. A respiratory mask and headgear combination according to claim 18 wherein the overlying strap has one or more guides through which the release cord passes, such that a distal end of the release cord is located in use at the front of the wearer and may be pulled to actuate release of the fastening means.

21. A respiratory mask and headgear combination according to claim 20 wherein in use a force acting on the headgear due to pulling of the cord acts to retain said other strap against the wearer's head whilst pulling away the overlying strap.

22. A respiratory mask and headgear combination according to claim 21 wherein in use further pulling of the cord in substantially the same direction acts to remove the headgear and mask from the wearer.

* * * * *